(12) United States Patent
Ly et al.

(10) Patent No.: US 10,025,971 B2
(45) Date of Patent: Jul. 17, 2018

(54) FRACABILITY MEASUREMENT METHOD AND SYSTEM

(71) Applicant: CGG SERVICES SA, Massy (FR)

(72) Inventors: Chi Vihn Ly, Katy, TX (US); Graham Spence, Conwy (GB)

(73) Assignee: CGG SERVICES SAS, Massy (FR)

( * ) Notice: Subject to any disclaimer, the term of this patent is extended or adjusted under 35 U.S.C. 154(b) by 0 days.

(21) Appl. No.: 14/898,516

(22) PCT Filed: Jun. 26, 2014

(86) PCT No.: PCT/EP2014/063587
§ 371 (c)(1),
(2) Date: Dec. 15, 2015

(87) PCT Pub. No.: WO2014/207137
PCT Pub. Date: Dec. 31, 2014

(65) Prior Publication Data
US 2017/0016873 A1    Jan. 19, 2017

Related U.S. Application Data

(63) Continuation-in-part of application No. 14/156,719, filed on Jan. 16, 2014, now Pat. No. 9,613,253.
(Continued)

(51) Int. Cl.
*G06K 9/00*    (2006.01)
*E21B 47/00*    (2012.01)
(Continued)

(52) U.S. Cl.
CPC .......... *G06K 9/00127* (2013.01); *E21B 47/00* (2013.01); *G01N 23/2251* (2013.01);
(Continued)

(58) Field of Classification Search
USPC ....... 382/100, 103, 106–107, 153, 162, 168, 382/173, 181, 190–194, 199, 209, 219,
(Continued)

(56) References Cited

U.S. PATENT DOCUMENTS

| 4,868,883 A * | 9/1989 | Chen ................. G06K 9/00127 |
| | | 382/109 |
| 6,088,656 A | 7/2000 | Ramakrishnan et al. |

(Continued)

FOREIGN PATENT DOCUMENTS

WO    2009126609 A2    10/2009

OTHER PUBLICATIONS

First Office Action in corresponding Chinese Application No. 201480042670.8 dated Feb. 27, 2017. (Both references were made of record in an Information Disclosure Statement dated Dec. 15, 2015.).

(Continued)

*Primary Examiner* — Seyed Azarian
(74) *Attorney, Agent, or Firm* — Patent Portfolio Builders PLLC

(57) ABSTRACT

A method for estimating a fracability index for a geological location includes determining a fabric metric and a mineralogical composition metric for a geological sample extracted from a geological location and estimating a fracability index for the geological location from the fabric metric and the mineralogical composition metric. The fabric metric may be a grain related measurement such as grain size or angularity, or a pore-space related measurement such as pore area, diameter, aspect ratio, and circumference, or statistics associated with such measurements. In certain embodiments, determining the mineralogical composition metric includes detecting a prevalence of at least one organic proxy within the geological sample such as vanadium, iron, (Continued)

uranium, thorium, copper, sulfur, zinc, chromium, nickel, cobalt, lead and molybdenum. Determining the mineralogical composition metric may also include detecting a prevalence of one, two, or all of siliciclastics, carbonate and clay.

15 Claims, 10 Drawing Sheets

Related U.S. Application Data

(60) Provisional application No. 61/839,934, filed on Jun. 27, 2013, provisional application No. 61/839,932, filed on Jun. 27, 2013.

(51) Int. Cl.
G01N 33/24 (2006.01)
G01N 23/2251 (2018.01)
G06T 7/00 (2017.01)
G01V 1/40 (2006.01)

(52) U.S. Cl.
CPC ........... G01N 33/24 (2013.01); G01N 33/241 (2013.01); G06K 9/0014 (2013.01); G06K 9/0063 (2013.01); G06T 7/0004 (2013.01); H05K 999/99 (2013.01); G01N 2223/401 (2013.01); G06T 2207/30181 (2013.01)

(58) Field of Classification Search
USPC ........ 382/232, 254–255, 266, 274, 285–291, 382/305, 312, 109; 348/46; 702/13; 703/1; 175/17; 75/343
See application file for complete search history.

(56) References Cited

U.S. PATENT DOCUMENTS

| 8,792,303 | B2 | 7/2014 | Downton et al. | |
|---|---|---|---|---|
| 2005/0087037 | A1* | 4/2005 | Abercrombie | C22B 1/00 75/343 |
| 2007/0203677 | A1 | 8/2007 | Awwiller | |
| 2011/0004448 | A1* | 1/2011 | Hurley | G06T 17/00 703/1 |
| 2011/0181701 | A1* | 7/2011 | Varslot | G06T 7/0026 348/46 |
| 2012/0316789 | A1* | 12/2012 | Suarez-Rivera | E21B 49/00 702/13 |
| 2013/0264118 | A1* | 10/2013 | Wideman | E21B 7/14 175/17 |
| 2015/0000903 | A1 | 1/2015 | Ly et al. | |

OTHER PUBLICATIONS

Office Action received in corresponding Chinese Application No. 201480042670.8, dated Aug. 8, 2017. All references not cited herewith have been previously made of record.

International Search Report in related International Application No. PCT/EP2014/063587, dated Feb. 4, 2015.

Written Opinion of the International Searching Authority in related International Application No. PCT/EP2014/063587, dated Feb. 4, 2015.

N. Gupta, et al., "Integrated petrophysical characterization of the Woodford Shale in Oklahoma", Society of Petrophysicists and Well-Log Analysts, Jun. 16, 2012.

D.M. Jarvie, et al., "Unconventional shale-gas systems: The Mississippian Barnett Shale of north-central Texas as one model for thermogenic shale-gas assessment", AAPG Bulletin, Apr. 2007, vol. 91, No. 4, pp. 475-499.

Chen Ji, et al.; "Mineral composition and brittleness of three sets of Paleozoic organic-rich shales in China south area"; Journal of China Coal Society, vol. 38, No. 5; May 2013; pp. 822-826.

Office Action in corresponding Chinese Application No. 2018011201549230 dated Jan. 17, 2018.

Examination Report in corresponding Australian Application No. 2014301059 dated May 22, 2017. (Both references, D1 and D2, were previously made of record by the Examiner on Jan. 3, 2017).

* cited by examiner

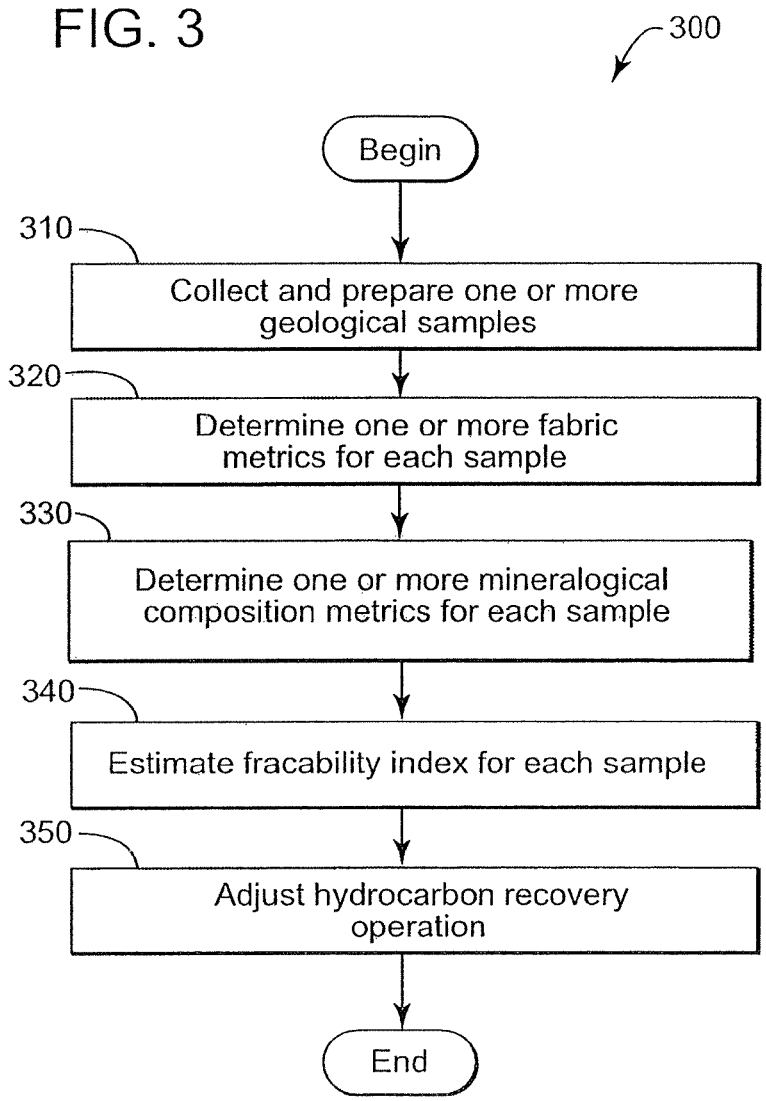

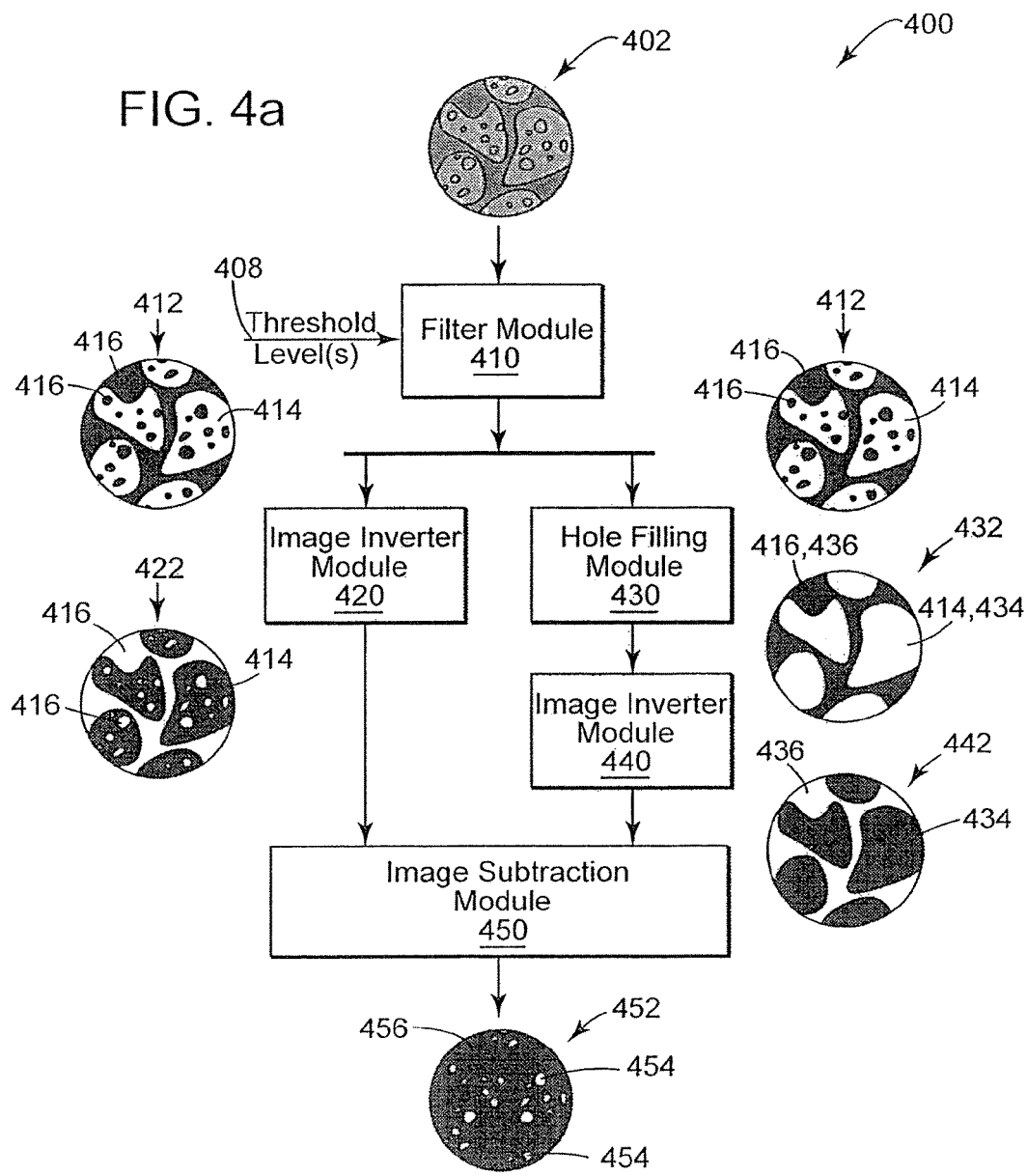

FIG. 6a

| ID | Area μm² | Feret Max Diameter μm | Feret Min Diameter μm |
|---|---|---|---|
| 2008801 | 0.92 | 096 | 0.96 |
| 2008800 | 6.45 | 3.99 | 1.92 |
| 2008798 | 4.6 | 3.1 | 1.92 |
| 2008797 | 11.97 | 6.13 | 2.84 |
| 2008796 | 10.13 | 4.42 | 2.88 |
| 2008795 | 12.89 | 5.25 | 2.88 |
| 2008794 | 12.89 | 5.76 | 3.62 |
| 2008793 | 25.78 | 8.45 | 5.03 |
| 2008792 | 0.92 | 0.96 | 0.96 |
| 2008791 | 17.5 | 6.8 | 3.84 |
| 2008790 | 15.65 | 5.76 | 3.84 |
| 2008788 | 9.21 | 3.99 | 2.88 |
| 2008787 | 4.6 | 3.1 | 1.92 |
| 2008786 | 13.81 | 7.03 | 3.03 |
| 2008785 | 1.84 | 1.92 | 0.96 |
| 2008784 | 7.37 | 3.67 | 2.88 |
| 2008783 | 8.29 | 3.67 | 2.88 |
| 2008782 | 11.05 | 5.25 | 2.88 |
| 2008781 | 8.29 | 4.42 | 2.8 |
| 2008778 | 36.84 | 15.48 | 3.84 |
| 2008777 | 4.6 | 3.1 | 1.92 |
| 2008776 | 23.02 | 8.45 | 4.95 |
| 2008775 | 11.97 | 4.42 | 3.84 |
| 2008774 | 12.89 | 5.85 | 2.88 |

FRACABILITY MEASUREMENT METHOD AND SYSTEM

BACKGROUND

Technical Field

Embodiments of the subject matter disclosed herein generally relate to the field of hydrocarbon prospecting and extraction. In particular, the embodiments disclosed herein relate to apparatuses, methods, and systems for determining the geo-mechanical properties of rock and adjusting hydrocarbon recovery operations in response to those measurements.

Discussion of the Background

Geophysical data is useful for a variety of applications such as weather and climate forecasting, environmental monitoring, agriculture, mining, and seismology. As the economic benefits of such data have been proven, and additional applications for geophysical data have been discovered and developed, the demand for localized, high-resolution, and cost-effective geophysical data has greatly increased. This trend is expected to continue.

For example, seismic data acquisition and processing may be used to generate a profile (image) of the geophysical structure under the ground (either on land or seabed) that facilitates finding and extracting hydrocarbon reserves. While this profile does not provide an exact location for oil and gas reservoirs, it suggests, to those trained in the field, the presence or absence of such reservoirs.

Traditionally, a land seismic survey system 10 capable of providing a high-resolution image of the subsurface of the earth is generally configured as illustrated in FIG. 1 (although many other configurations are used). System 10 includes plural receivers 12 and acquisition units 12a positioned over an area 13 of a subsurface to be explored and in contact with the surface 14 of the ground. A number of seismic sources 16 are also placed on surface 14 in an area 17, in a vicinity of area 13 of receivers 12. A recording device 18 is connected to a plurality of receivers 12 and placed, for example, in a station-truck 20. Each source 16 may be composed of a variable number of vibrators or explosive devices, and may include a local controller 22. A central controller 24 may be present to coordinate the shooting times of the sources 16. A positioning system 26 (e.g. GPS, GLONASS, Galileo, and Beidou) may be used to time-correlate sources 16 and receivers 12 and/or acquisition units 12a.

With this configuration, the sources 16 are controlled to generate seismic waves, and the receivers 12 record the waves reflected by the subsurface. The receivers 12 and acquisition units 12a may be connected to each other and the recording devices with cables 30. Alternatively, the receivers 12 and acquisition units 12a can be paired as autonomous nodes that do not need the cables 30.

The purpose of seismic imaging is to generate high-resolution images of the subsurface from acoustic reflection measurements made by the receivers 12. Conventionally, as shown in FIG. 1, the plurality of seismic sources and receivers is distributed on the ground surface at a distance from each other. The sources 16 are activated to produce seismic waves that travel through the subsoil. These seismic waves undergo deviations as they propagate. They are refracted, reflected, and diffracted at the geological interfaces of the subsoil. Certain waves that have travelled through the subsoil are detected by the seismic receivers 12 and are recorded as a function of time in the form of signals (called traces).

Once a promising region for hydrocarbon reserves is found, vertical and horizontal wells may be drilled to potentially extract the reserves. For example, in the United States and other regions of the world, there are many areas where oil shale rock deposits are to be found. Oil shale is a form of sedimentary deposits that were laid down eons ago, typically in the form of calcium carbonates, sodium carbonates, calcium bicarbonates, and quartz. Furthermore, soil materials and other compounds may have been entrapped in the matrix of the aforementioned materials.

While many oil shale reserves exist, most of them are located as deep deposits five to ten thousand feet below the surface of the earth. Since the early $20^{th}$ century, many attempts have been made to mine or extract the oil from stratified shale formations. Although historically the shale oil proved to be a very suitable hydrocarbon product, the complexity of extracting oil shale reserves increased the cost of production well beyond the market price of similar products. Consequently, sustained shale production proved to be uneconomical.

Recently, the rapid development and exploitation of two specialized technologies has dramatically changed the cost of extracting oil from shale rock deposits. The first improvement is the carefully controlled and steerable directional drilling techniques that enable vertical drilling to be redirected into horizontal drilling at a selected depth. The drilling can then continue horizontally in a shale formation for a considerable distance.

The second improvement was the development of hydraulic fracturing techniques where slurry is pumped into a well at regular perforation points along an inserted casing in order to extend the economic life of the depleting oil fields. Although first used in the late 1940's, hydraulic fracturing has recently become a common technique to enhance the production of low-permeability formations, especially unconventional reservoirs—primarily tight sands, coal beds, and deep shales.

Despite many improvements, the cost of fracturing is still relatively high and significant inefficiencies remain. For example, many oil shale formations cross tectonic fault lines in the crust of the earth and thus can be discontinuous in their configuration. Some oil shale formations are slightly inclined in both the vertical and horizontal planes. Consequently, the abundance of oil may vary significantly as a function of drilling distance. In fact, it is estimated that approximately 30 percent of the perforation points in a typical fracturing operation correspond to dry regions where oil is unavailable.

Referring to FIG. 2a, in horizontal shale gas wells, fracturing is typically done in multiple stages at regular fixed intervals starting at the "toe" of the well (the name given to the tip of the foot-shaped horizontal wellbore) and proceeding toward the "heel" (the end of the horizontal section of the wellbore that is closest to the vertical portion). For example, a wellbore that extends 5,000 feet laterally within a shale layer might be hydraulically fractured in ten to fifteen stages several hundred feet apart. Typically, each perforation interval is isolated in sequence so that only a single section of the well is hydraulically fractured at a given time and to prevent damage to other sections of the wellbore.

During a hydraulic fracturing operation, fracturing fluid is pumped at high pressure through perforations in the section of the casing. The chemical composition of the fracturing fluid, as well as the rate and pressure at which it is pumped into the shale formation, are tailored to the specific properties of each shale and, to some extent, each well. When the pressure increases to a sufficient level, a planar hydraulic fracture opens in the rock, propagating more or less perpendicularly to the path of the wellbore. Although the fractures depicted in FIG. 2a are by necessity shown to be substantially vertical, the casing perforations in a well are typically oriented to produce fractures that propagate horizontally rather than vertically.

It should be noted that the fracturing characteristics of shale rock may vary significantly between wells or even within the same well. For example, soft oil shale formations respond differently than hard oil shale formations when subjected to the same level of hydraulic water pressure and soaking time. In addition to the mineral composition, the fracturing characteristics of shale formations may be dependent on the texture or fabric of the shale rock. For example, shale formations with larger and/or more abundant pores may fracture more easily than shale formations with smaller and less abundant pores.

Referring to FIG. 2b, a typical hydro-fracture may propagate horizontally about 500-800 feet away from the well in each direction. The fracturing pressure is carefully controlled to prevent vertical propagation beyond the thickness of the layer of gas-producing shale. The pressure needed to propagate the hydraulic fracture varies and depends on depth, the pressure of the gas in the pores of the shale, and the geo-mechanical properties of the hydrocarbon bearing layer, such as porosity.

Given the foregoing, reliable, and readily available estimates of the fracability of the hydrocarbon bearing layer, as well as adjacent layers, could significantly improve the effectiveness of hydrocarbon recovery operations.

SUMMARY

A method for estimating a fracability index for a geological location includes determining a fabric metric and a mineralogical composition metric for a geological sample extracted from a geological location and estimating a fracability index for the geological location from the fabric metric and the mineralogical composition metric. The fabric metric may be a grain related measurement such as grain size or angularity, or a pore-space related measurement such as pore area, diameter, aspect ratio, and circumference, or statistics associated with such measurements.

In certain embodiments, determining the mineralogical composition metric includes detecting a prevalence of at least one organic proxy within the geological sample such as vanadium, iron, uranium, thorium, copper, sulfur, zinc, chromium, nickel, cobalt, lead, and molybdenum. Determining the mineralogical composition metric may also include detecting a prevalence of one, two, or all of siliciclastics, carbonate, and clay.

The method may also include adjusting a hydrocarbon recovery operation according to the fracability index. In certain embodiments, the equipment used to determine the fabric metric and the mineralogical composition metric and estimate the fracability index are located onsite to facilitate responsive adjustment of the hydrocarbon recovery operations. A corresponding system and apparatus are also disclosed herein.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 3 is a flowchart diagram depicting one embodiment of a measurement and adjustment method for hydrocarbon recovery operations;

FIG. 4a is a dataflow diagram depicting one embodiment of a pore-space image generation apparatus;

FIG. 6a is a table showing one example of results obtained with embodiments disclosed herein;

DETAILED DESCRIPTION

Figure 1:
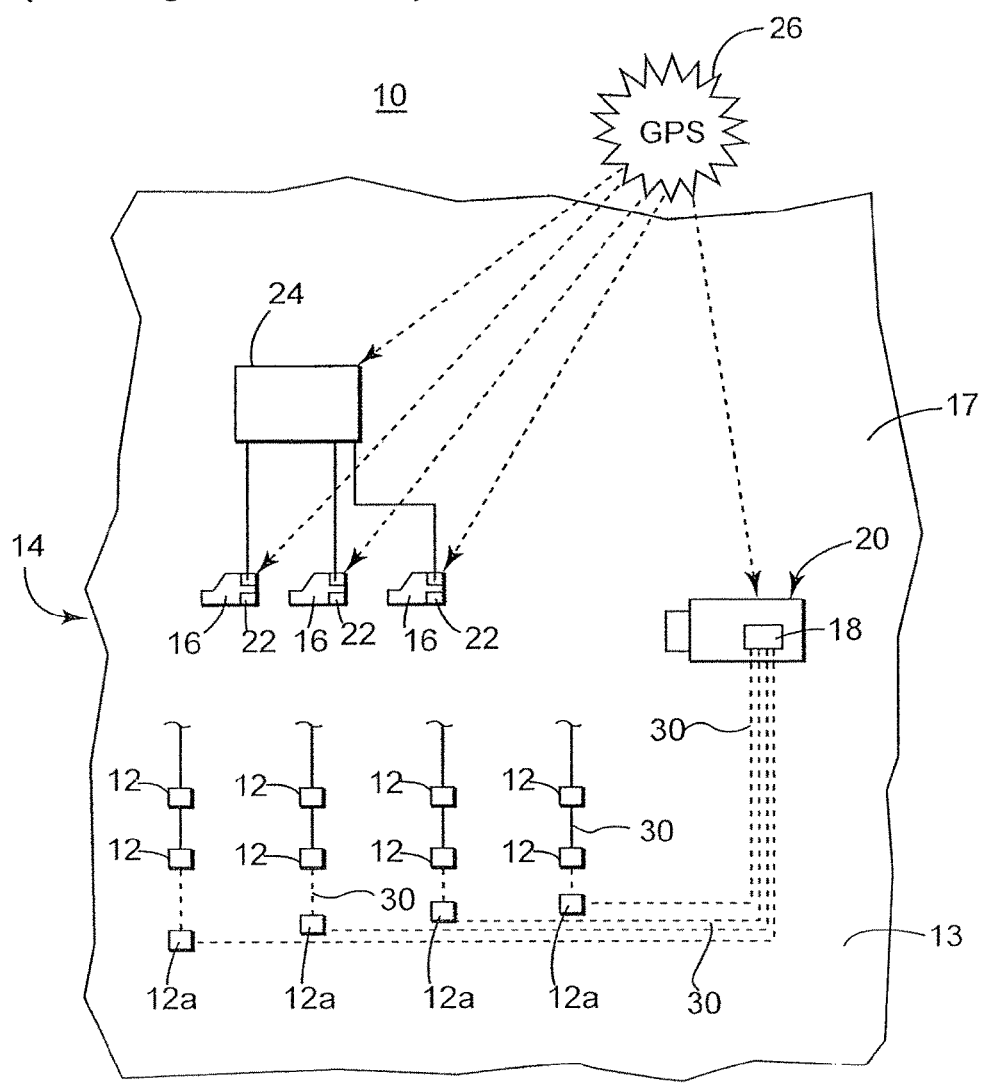
FIG. 1 is a schematic diagram depicting a traditional land seismic survey system used in a prospecting phase for hydrocarbon recovery operations.
Figure 2A:
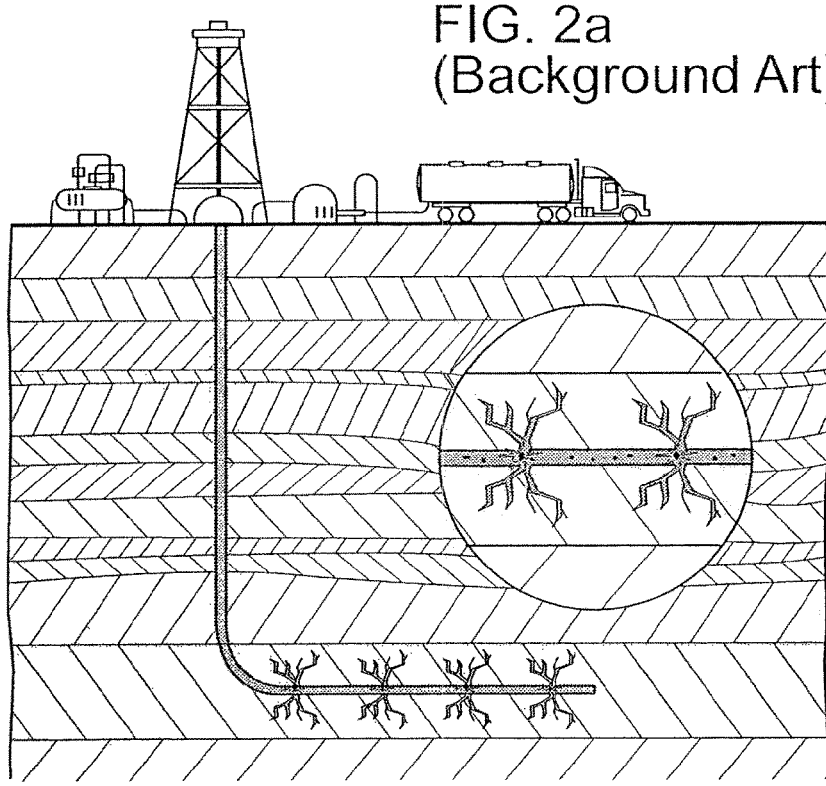
FIGS. 2a and 2b are schematic diagrams depicting the use of fracturing to improve an extraction phase of hydrocarbon recovery operations.
Figure 2B:
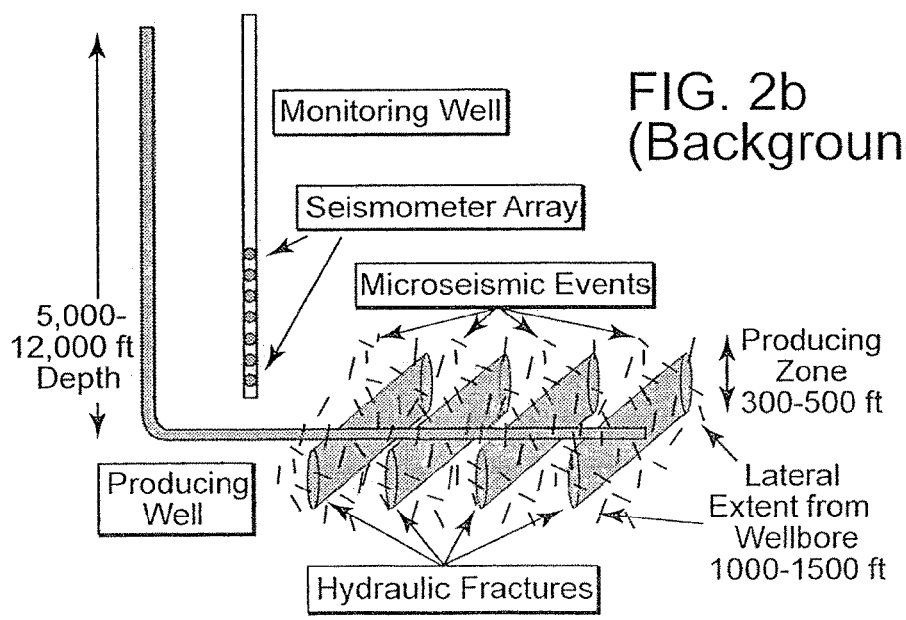

The following description of the exemplary embodiments refers to the accompanying drawings. The same reference numbers in different drawings identify the same or similar elements. The following detailed description does not limit the invention. Instead, the scope of the invention is defined by the appended claims.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures, or characteristics may be combined in any suitable manner in one or more embodiments.

As used herein the term "index" refers to a measurement derived value that describes the strength of a particular characteristic or attribute of an object including a value derived from processing various measurements for an object including including weighted combinations of measurements and measurement related statistics for the object. Similarly, the term "metric" refers to a measurement of a particular characteristic or attribute of an object or an index derived from multiple measurements related to a characteristic or attribute of an object. For example, multiple and repeated measurements may be obtained for geological samples and used or processed to provide one or more fabric metrics and one or more mineralogical composition metrics for the samples.

As mentioned in the background section, providing a timely and accurate characterization of the fracability of rock at specific geophysical locations could significantly improve both the exploration and extraction phases of hydrocarbon recovery operations. As detailed herein, one or more fabric metrics that describe the fabric related characteristics of geological samples, and one or more mineralogical composition metrics that describe the mineralogical characteristics of geological samples are used to determine a fracability index for geological samples and adjust hydrocarbon recovery operations.

FIG. 3 is a flowchart diagram depicting one embodiment of a measurement and adjustment method 300 for hydrocarbon recovery operations. As depicted, the method 300 includes collecting and preparing (310) one or more geological samples, determining (320) one or more fabric metrics for each sample, determining (330) one or more mineralogical composition metrics for each sample, estimating (340) a fracability index for each sample, and adjusting (350) a hydrocarbon recovery operation. The method may be conducted in conjunction with finding and extracting hydrocarbons from a known or unknown hydrocarbon reserve.

Collecting and preparing (310) one or more geological samples may include retrieving core extractions and/or cutting remnants and preparing geological samples therefrom in a manner known to those of skill in the art. For example, the extractions and/or remnants may be cut, broken, or crushed to obtain fragments of a suitable size. Some or all of the suitably sized fragments may then be encased in a suspension media to form samples of a common shape suitable for imaging or making other measurements. Examples of suspension media include epoxy, wax, binding powder, plastic, and resin. The commonly shaped samples may also be cut and/or polished to provide a planar face that facilitates imaging and analysis. Preparing the samples may also include treating the samples to cause the pores or grains of the samples to stand out. For example, samples may be treated with a dye such as a fluorescent dye or a non-fluorescent dye that accentuates the pores or the grains.

Determining (320) one or more fabric metrics for each sample may include making grain related measurements and/or pore-space related measurements, or obtaining such measurements, or indices and/or statistics for such measurements. Examples of grain related measurements include grain area, diameter, circumference, aspect ratio, angularity, and the like. Examples of pore-space related measurements include pore area, diameter, aspect ratio, and circumference. In some embodiments, multiple and repeated grain related and pore-space related measurements are averaged, weighted, or statistically processed in some other way know to those of skill in the art of data processing to provide the fabric metrics for a sample.

The fabric metric and/or the mineralogical composition metric may be determined from measurements provided by one or more electromagnetic probing tools such as a SEM imaging tool, an optical imaging tool, an x-ray tool, spectral analysis tool and elemental analysis tool. Image processing may also be utilized in determining the fabric metric and the mineralogical composition metric.

Determining (330) one or more mineralogical composition metrics for each sample may include using SEM-BSE imaging, x-ray imaging, chemical testing, spectral imaging, optical imaging, and the like to make mineralogical composition measurements. Determining (330) may also include obtaining or processing such measurements. Similar to the determining operation 320, multiple and repeated measurements may be taken and averaged, weighted, or statistically processed in some other way known to those of skill in the art of data processing.

In certain embodiments, determining (330) a mineralogical composition metric for the geological sample includes detecting a prevalence of at least one organic proxy within the geological sample such as vanadium, iron, uranium, thorium, copper, sulfur, zinc, chromium, nickel, cobalt, lead and molybdenum. In some embodiments, determining (330) a mineralogical composition metric for the geological sample includes detecting a prevalence of one, two, or all three of, siliciclastics, carbonate, and clay.

Estimating (340) a fracability index for each sample may include normalizing and weighting each of the fabric metrics and each of the mineralogical composition metrics to provide a fracability index. The fracability index may correspond to the amount of fracking pressure that is required to break apart rock similar to the geological sample. In one embodiment, the weighting of each metric is determined by correlating the fabric and mineralogical composition metrics with specific geo-mechanical properties such as brittleness, rock fabric characteristics, pore fabric characteristics, strength, permeability, organic content saturation, liquid saturation, capillary pressure, and stress fields for a set of reference samples. One of skill in the art may appreciate that the fabric metrics and the mineralogical composition metrics may be readily correlated to various geo-mechanical properties via experimentation, or via published data or formulas such as the brittleness formula of Jarvie et al. See, for example, AAPG Bulletin, v. 91, no. 4 (April 2007), pp. 475-499 which is incorporated herein by reference.

Adjusting (350) a hydrocarbon recovery operation may include making adjustments that improve the hydrocarbon recovery operation. Examples of improvement include increasing throughput, improving quality, lowering cost, improving safety, and the like. Examples of hydrocarbon recovery operations include prospecting, exploration, conducting seismic surveys, drilling, mining, fracking, pumping, and remediation. In one embodiment, adjusting (350) a hydrocarbon recovery operation includes determining a preferred location for a fracking perforation and placing a fracking perforation proximate to the preferred location. In certain embodiments, the equipment used to determine the fabric metric and the mineralogical composition metric are located onsite to facilitate responsive adjustment of the hydrocarbon recovery operations.

In some embodiments, seismic data is leveraged to determine the fracability index and adjust hydrocarbon recovery operations. For example, an inversion workflow process for seismic data (not to be confused with image inversion as discussed herein) may be leveraged along with fabric metrics and mineralogical composition metrics to determine the fracability index. For more information on inversion workflow processes see U.S. Provisional Patent Application 61/876,864 entitled "Integration of surface seismic, microseismic, mineralogy and rock properties" and U.S. patent application Ser. No. 13/046,447 entitled "Methods and systems for performing azimuthal simultaneous elastic inversion". Each of these references is incorporated herein by reference.

Figure 4B:
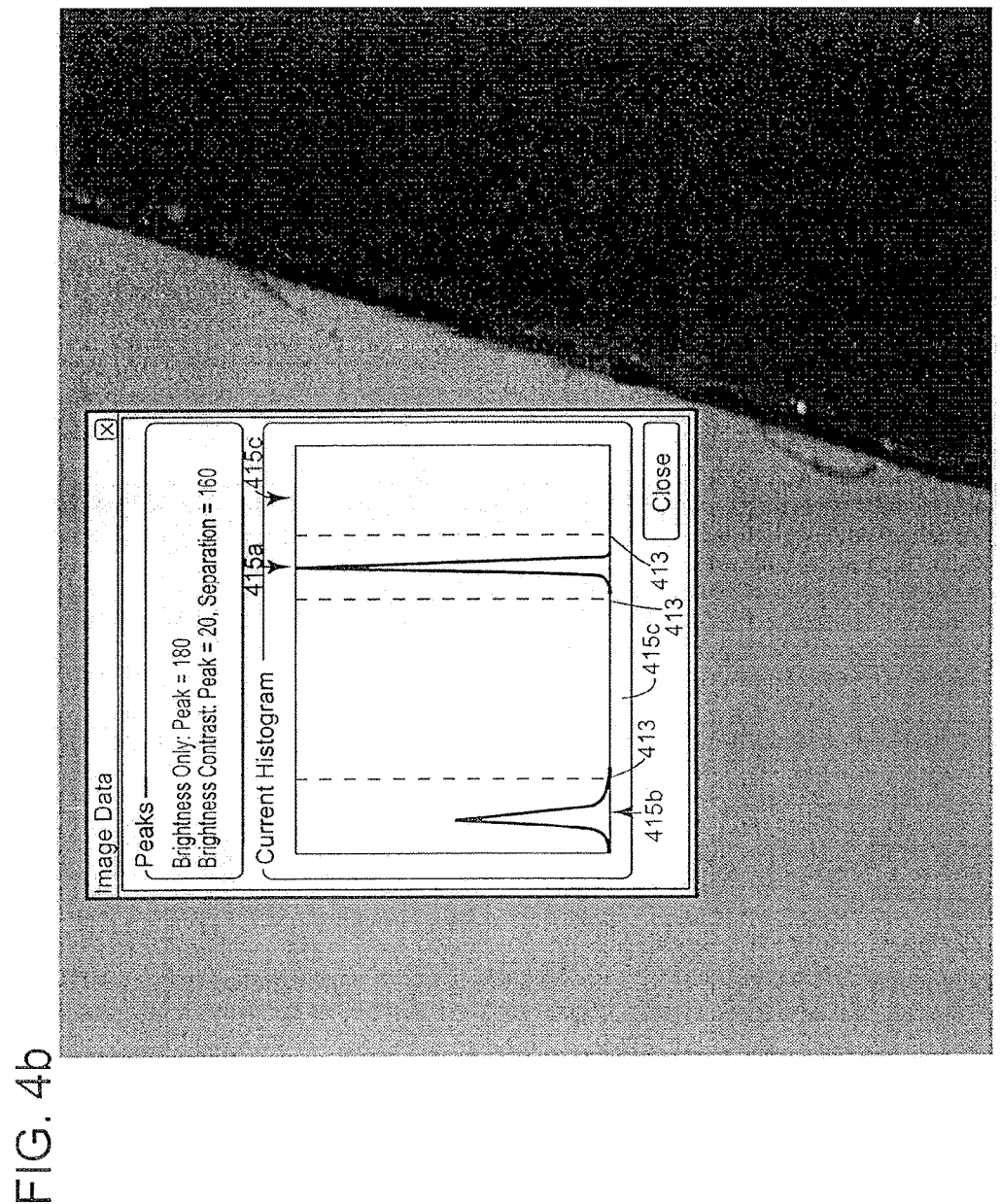
FIG. 4b is a screenshot showing how histogram information can be leveraged to set threshold levels for image processing operations.
Figure 5:
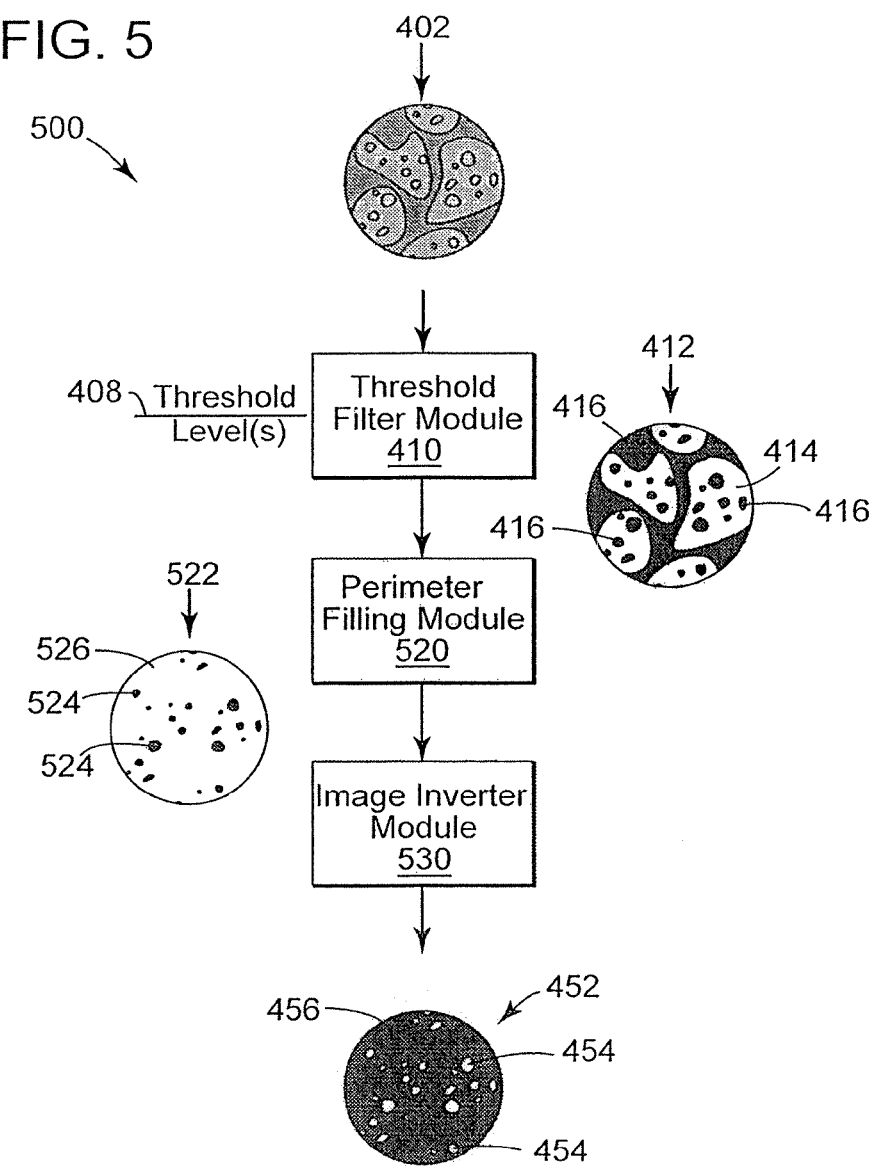
FIG. 5 is a dataflow diagram depicting another embodiment of a pore-space image generation apparatus.

FIGS. 4*a*, 4*b*, and 5 provide additional details on measuring pore-space metrics for geological samples as is also described in co-pending U.S. patent application Ser. No. 14/156,719 referenced above and incorporated herein by reference. The pore-space metrics may be utilized as fabric metrics along with mineralogical composition metrics to estimate the fracability of geological locations corresponding to geological samples.

FIG. 4*a* is a dataflow diagram depicting one embodiment of a pore-space image generation apparatus 400. As depicted, the pore-space image generation apparatus 400 includes a threshold filter module 410, an image inverter module 420, a hole filling module 430, an image inverter module 440, and an image subtraction module 450. The depicted modules may be image processing modules that operate on digital images comprised of pixels.

In some embodiments, the modules depicted in FIG. 4a (and also FIG. 5) are standard image processing modules or functions that are available in open source software programs such as SIP, GIMP, and FIJI, commercial image processing software programs such as Adobe Photoshop® (operating in batch mode) or general technical computing programs such as MATLAB®. In other embodiments, one or more of the modules depicted in FIG. 4a may be custom developed software that executes on a computing device. The images processed by the depicted modules may be digital images comprised of, or convertible to, pixels that have one or more values associated therewith such as intensity, hue, and saturation or similar values common to image processing. For example, the pixels may be greyscale pixels that have intensity values that correspond to back-scattering rates detected by an SEM imaging device.

The threshold filter module 410 may receive a sample image 402 and filter the image according to one or more threshold levels 408 to provide a mineral image 412 comprising mineral (i.e., rock) regions 414 and non-mineral (i.e., non-rock) regions 416. The threshold levels may be selected to distinguish the mineral regions 414 from the non-mineral regions 416. For example, pixels of the sample image 402 with intensity values that exceed a selected threshold may be set by the threshold filter module 410 to a value that indicates that the pixel is a mineral region pixel. Other pixels may be set to a value that indicates that the pixel is a non-mineral region pixel. The pixels may be clustered to form the regions 414 and 416. In the embodiment depicted in FIG. 4a, the mineral regions 414 are shown in white and the non-mineral regions 416 (corresponding to void spaces and suspension media regions) are shown in dark gray.

In some embodiments, multiple threshold levels 408 are provided and only pixels within a certain range of are assigned to be mineral region pixels by the filter module 410. One of skill in the art will appreciate that potentially noisy images may be processed by providing two or more threshold levels that are used by the threshold filter module 410 to partition the pixel intensity space into a mineral range, a non-mineral range, and one or more undetermined ranges resulting in mineral pixels, non-mineral pixels, and undetermined pixels within the mineral image 412. Consequently, isolated undetermined (i.e., noisy) pixels may be filtered out of the mineral image 412 with additional processing by the filter module 410. For example, FIG. 4b shows how histogram information for a calibration image, or the like, may be used to set multiple threshold levels 413 that partition the pixel intensity space into a mineral range 415a, a non-mineral range 415b, and two undetermined ranges 415c. Consequently, the likelihood of misidentifying a mineral pixel as a non-mineral pixel or vice versa is substantially eliminated.

Returning to FIG. 4a, the image inverter module 420 receives the mineral image 412 and inverts the image to provide a non-mineral image 422 where the non-mineral regions 416 (corresponding to void space and the suspension media) are highlighted. [The reader should be aware that image inversion is a pixel-by-pixel inversion of an image known to those of skill in the art of image processing and that image inversion is different than workflow inversion (mentioned above) which inverts a seismic data matrix through a matrix inversion operation known to those of skill in the art of seismic data processing.] The hole filling module 430 fills non-mineral regions that are completely encompassed by a mineral region to provide a rock region mask 432 comprising rock regions 434 and suspension media regions 436. In one embodiment, the hole filling module 430 scans the mineral image 414 and detects a pixel span corresponding to a hole by detecting a mineral to non-mineral transition followed by a non-mineral to mineral transition. The detected pixel span is then converted to mineral pixels to fill the hole. Subsequently, the filled mineral regions 414 are identified as rock regions 434 and the remaining non-mineral regions 416 are identified as suspension media regions 436.

The image inverter module 430 receives the rock region mask 432 and inverts the image to provide a suspension media mask 442 where the suspension media regions 436 are highlighted. The image subtraction module (alternatively masking module) 450 subtracts the suspension media mask 442 from the non-mineral image 422 to provide the pore-space image 452 comprising pore-space regions 454 and non-pore regions 456. The pore-space image 452 may be used to calculate one or more pore-space metrics for the geological sample capture within the sample image 402.

One of skill in the art will appreciated that the pore-space image may be generated from the sample image with a wide variety of techniques and that the preferred approach may be dependent on the image processing functions (i.e., modules) that are readily available within an image processing library or the like.

FIG. 5 is a dataflow diagram depicting one embodiment of pore-space image generation apparatus 500. As depicted, the pore-space image generation apparatus 500 includes the threshold filter module 410 described above as well as a perimeter filling module 520, and an image inverter module 530. The pore-space image generation apparatus 500 is one example of an alternative embodiment to the pore-space image generation apparatus 400 depicted in FIG. 4a.

The perimeter filling module 520 receives the mineral image 412 and provides a negative pore-space image 522 comprising pore-space regions 524 and non-pore regions 526. In one embodiment, the perimeter filling module 520 determines suspension media pixel spans (not shown) within the horizontal scan lines of the image 412 by detecting non-mineral pixels at the edge of the mineral image 412 and advancing into the image until a mineral pixel is detected. The pixels of each suspension media pixel span (not shown) are then assigned to be non-pore region pixels along with all of the pixels within the mineral regions 414. The assigned non-pore region pixels collectively define the non-pore space regions 526. The remaining non-mineral region pixels are assigned to be pore-space pixels that collectively define the pore-space regions 524. The image inverter module 530 inverts the negative pore-space image 522 to provide the (positive) pore-space image 452.

One of skill in the art will appreciate that the functionality provided by the modules of the apparatus 400 and the apparatus 500 may be achieved with a variety of implementations. The functionality may be partitioned in a variety of ways resulting in a variety of modules that collectively provide the described functionality. The pore-space images generated therewith may be used to determine of variety of pore-space metrics and other results for the corresponding geological samples.

Figure 6B:
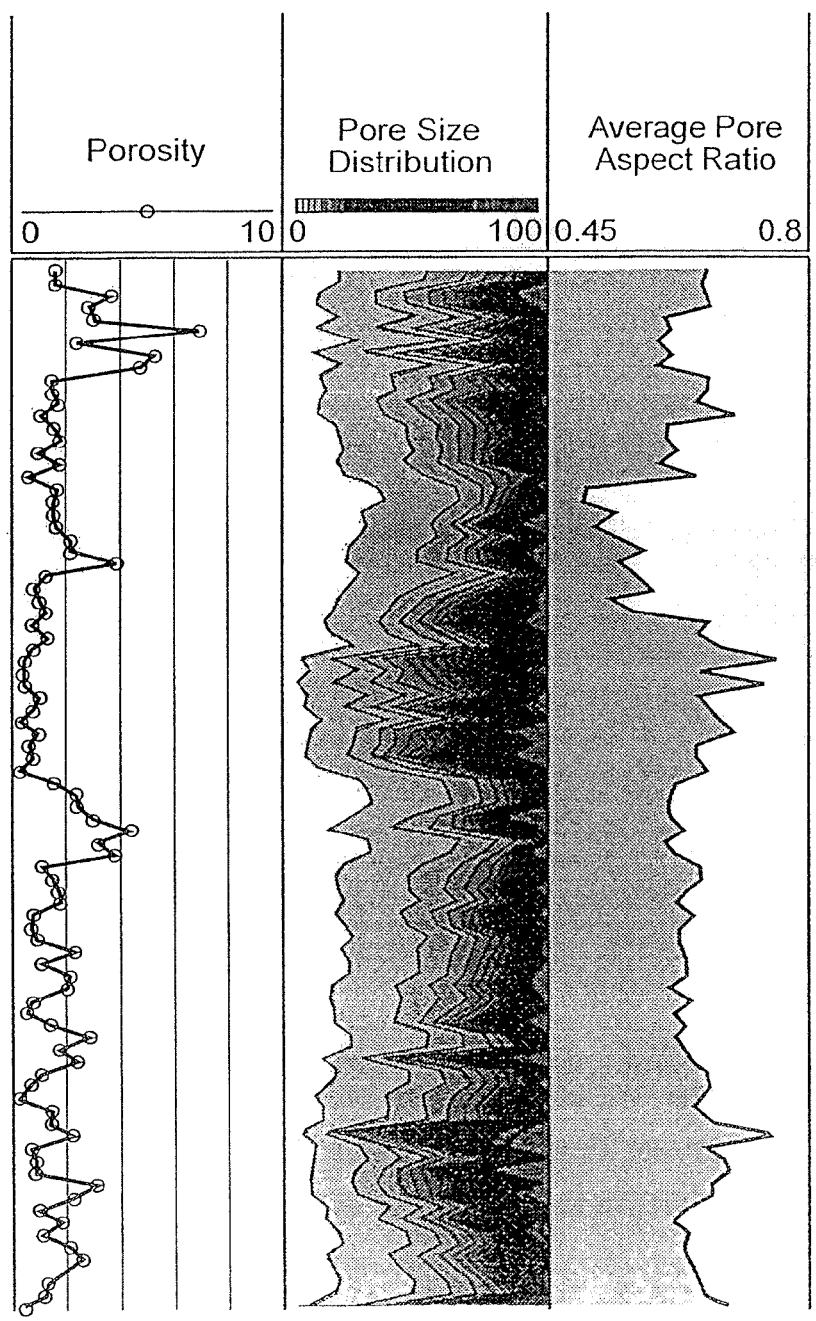
FIG. 6b is a graph showing another example of results obtained with embodiments disclosed herein.

FIG. 6a is a table showing one example of results obtained with embodiments disclosed herein and FIG. 6b is a graph showing another example of results obtained with embodiments disclosed herein. The table in FIG. 6a indicates the maximum and minimum diameter of pores (i.e., the ferret diameter) for each mineral region measured in one geological sample. The graph in FIG. 6b indicates the porosity, pore size distribution, and average pore aspect ratio for each mineral region measured in a geological sample. Much of the information shown in FIGS. 6a and 6b is not directly available with traditional geological measurement techniques. The information shown may be used to estimate a fracability index for geological samples and the geological locations from which the samples were taken.

Figure 6C:
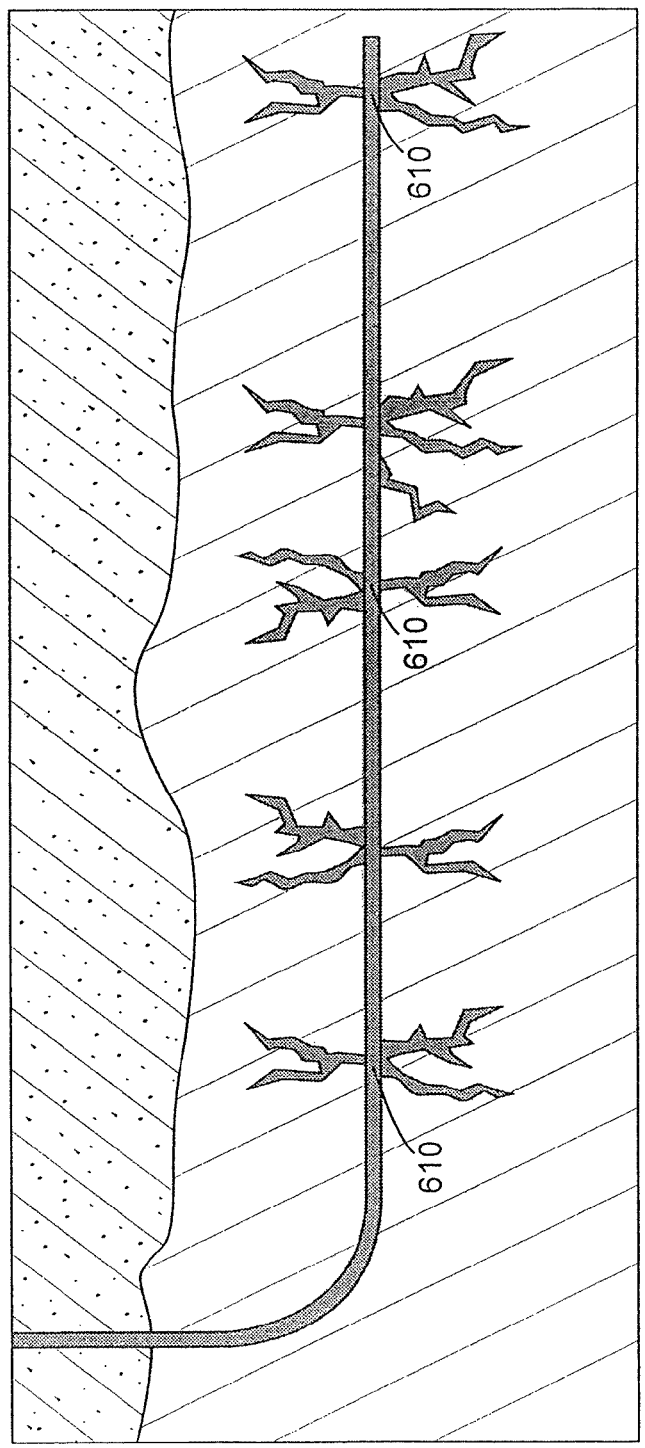
FIG. 6c is a schematic diagram depicting selected placement of fracturing perforations in response to measurements provided by embodiments disclosed herein.

FIG. 6c is a schematic diagram depicting selected placement of fracturing perforations according to the measurements provided by embodiments disclosed herein. Rather than placing the perforations at regular intervals, the perforation locations 610 can be selected based on actual measurements of the rock as a function of position or drilling distance.

The samples that are imaged may be core samples or cutting samples. The use of cutting samples may simplify and speed up the drilling phase of hydrocarbon recovery operations. The images used to measure the pore-space metrics may be SEM images, optical images, or the like. The pore-space metrics measured include a variety of measurements such as pore area, maximum pore diameter, minimum pore diameter, pore aspect ratio, pore circumference, porosity, and pore size distribution.

The images and/or the imaging equipment may be calibrated to provide consistent results. In certain embodiments, one or more image processing parameters such as brightness, contrast, and threshold values (e.g., the threshold levels 408) are manually or automatically adjusted. Calibration samples may be used to facilitate such adjustment. For example, with SEM imaging, one or more calibration samples comprising two or more materials with different average atomic numbers may be used for calibration of the imaging equipment. Examples of such materials could include, but are not limited to, metallic copper, quartz, gold, aluminum, epoxy resin, molybdenum, and manganese.

The SEM equipment may be calibrated so that the total number of electrons hitting the surface of the calibration samples is consistent with a predetermined value. This can be achieved by either direct measurement of the incident electron beam or by measurement of secondary emissions from the incident electron beam. The gain and amplitude of an amplifier associated with the SEM equipment such as an amplifier for a SEM backscatter diode may also be calibrated to obtain standard levels of brightness and contrast. To achieve this, the calibration samples may be used to provide two distinct grey level peaks, as measured by the SEM backscatter diode. The gain and amplitude settings on the backscatter amplifier may also be adjusted such that the distinct atomic weights for the various standard materials in the calibration samples generate predetermined greyscale levels.

When generating images on actual samples, the sample area may be segmented into a grid, and backscatter electron images may be collected from a predetermine number of grid spaces. Each of the collected backscatter electron images may then be processed using a thresholding filter as described above. The threshold value used by the thresholding filter may be set to a predetermined greyscale level that is between the expected greyscale level of the rock being imaged and the suspension media. With optical equipment, similar calibration and segmenting procedures may be used to provide consistent imaging results.

Figure 7:
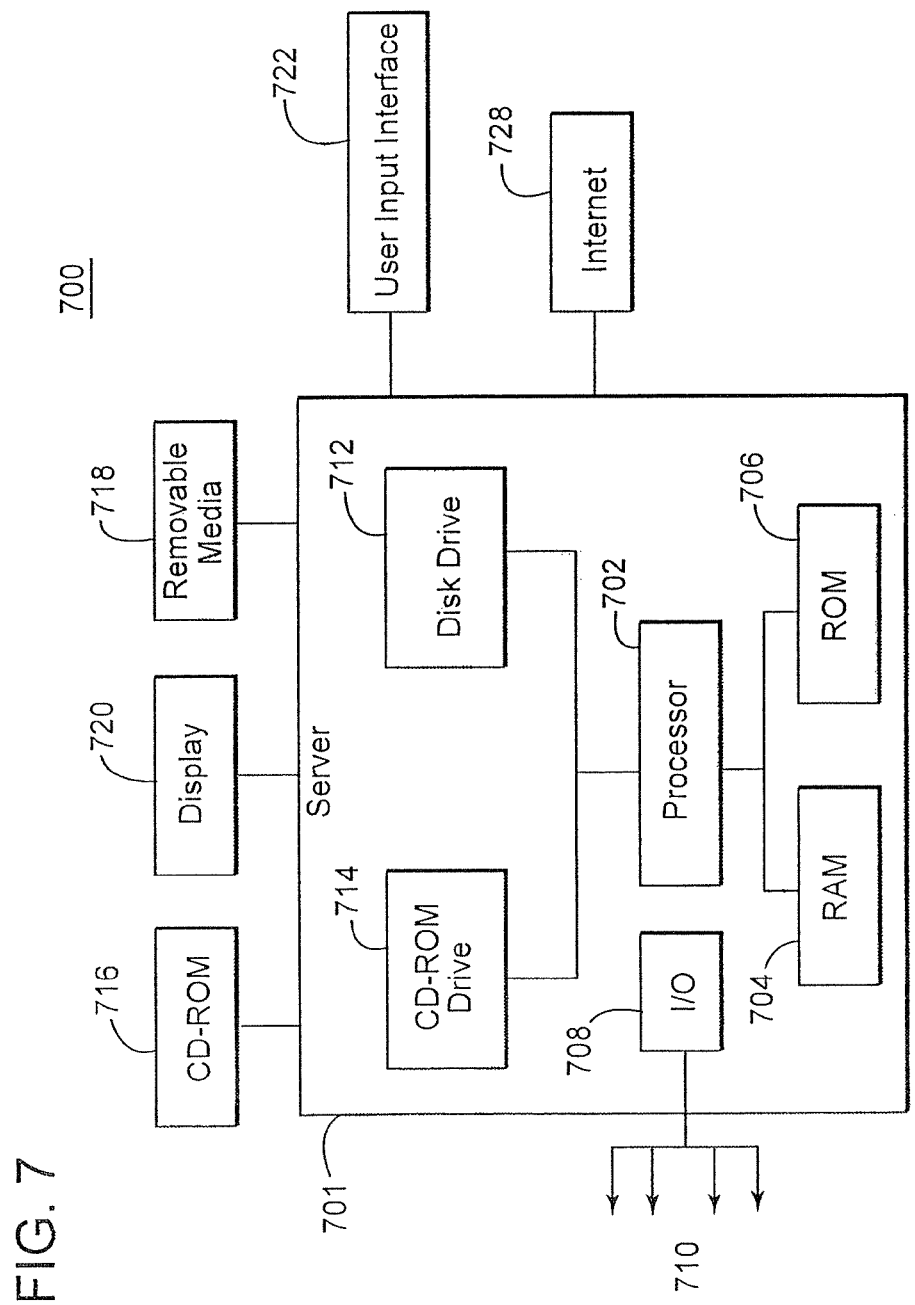
FIG. 7 is a block diagram of a computing device for processing images of geological samples.

The above-discussed procedures and methods may be implemented in a computing device illustrated in FIG. 7. Hardware, firmware, software or a combination thereof may be used to perform the various steps and operations described herein. The computing device 700 of FIG. 7 is one example of a computing structure that may be used in connection with such a system.

The computing device 700 suitable for performing the activities described in the embodiments described herein may include a server 701. Such a server 701 may include a central processor (CPU) 702 coupled to a random access memory (RAM) 704 and to a read only memory (ROM) 706. The ROM 706 may also be other types of storage media to store programs, such as programmable ROM (PROM), erasable PROM (EPROM), etc. The processor 702 may communicate with other internal and external components through input/output (I/O) circuitry 708 and bussing 710, to provide control signals and the like. The processor 702 carries out a variety of functions as are known in the art, as dictated by software and/or firmware instructions.

The server 701 may also include one or more data storage devices, including hard drives 712, CDDROM drives 714, and other hardware capable of reading and/or storing information such as DVD, etc. In one embodiment, software for carrying out the above-discussed steps may be stored and distributed on a CDDROM or DVD 716, a USB storage device 718 or other form of media capable of portably storing information. These storage media may be inserted into, and read by, devices such as the CDDROM drive 714, the disk drive 712, etc. The server 701 may be coupled to a display 720, which may be any type of known display or presentation screen, such as LCD displays, plasma display, cathode ray tubes (CRT), etc. A user input interface 722 is provided, including one or more user interface mechanisms such as a mouse, keyboard, microphone, touchpad, touch screen, voice-recognition system, etc.

The server 701 may be coupled to other devices, such as sources, detectors, etc. The server may be part of a larger network configuration as in a global area network (GAN) such as the Internet 728, which allows ultimate connection to the various landline and/or mobile computing devices.

In summary, the methods, apparatuses, and systems presented herein provide a number of distinct advantages over prior art methods, apparatuses, and systems. It should be noted that many of the functional units described herein such as those related to image processing are identified as modules. Others are assumed to be modules. One of skill in the art will appreciate that the various modules described herein may include a variety of hardware components that provide the described functionality including one or more processors such as CPUs or microcontrollers that are configured by one or more software components. The software components may include executable instructions or codes and corresponding data that are stored in a computer-readable storage medium such as a non-volatile memory, or the like. The instructions or codes may include machine codes that are configured to be executed directly by the processor. Alternatively, the instructions or codes may be configured to be executed by an interpreter, or the like, that translates the instructions or codes to machine codes that are executed by the processor.

It should also be understood that this description is not intended to limit the invention. On the contrary, the exemplary embodiments are intended to cover alternatives, modifications, and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A method for estimating a fracability index for a geological location, the method comprising:
    determining a fabric metric for a geological sample extracted from a geological location;
    determining a mineralogical composition metric for the geological sample;
    estimating a fracability index for the geological location from the fabric metric and the mineralogical composition metric; and
    adjusting a hydrocarbon recovery operation for the geological location according to the fracability index,
    wherein the determining of the fabric metric and/or the determining of the mineralogical composition metric use an electromagnetic probing tool, and
    the estimating includes normalizing and weighting each of the fabric metric and the mineralogic composition metric based on correlations of the fabric metric and the mineralogic composition metric with geo-mechanical properties of reference samples.

2. The method of claim 1, wherein the fabric metric comprises a pore-space metric.

3. The method of claim 1, wherein the fabric metric comprises a grain metric.

4. The method of claim 1, wherein determining the mineralogical composition metric for the geological sample comprises detecting a prevalence of at least one organic proxy within the geological sample.

5. The method of claim 1, wherein determining the mineralogical composition metric for the geological sample comprises detecting a prevalence of siliciclastics, carbonate, and clay.

6. The method of claim 1, wherein determining the fabric metric comprises image processing of an image of the geological sample.

7. The method of claim 6, wherein the image of the geological sample is an electron microscopy image.

8. The method of claim 6, wherein the image of the geological sample is an optical image.

9. The method of claim 1, wherein the adjusting of the hydrocarbon recovery comprises determining a location for a fracking perforation.

10. A system for estimating a fracability index for a geological location, the system comprising:
    an electromagnetic probing tool used in measuring at least one of a fabric metric and/or a mineralogical composition metric for a geological sample extracted from a geological location; and
    a computing device including a processor and configured to obtain the fabric metric and/or the mineralogical composition metric, to estimate a fracability index for the geological location from the fabric metric and the mineralogical composition metric, and to adjust a hydrocarbon recovery operation for the geological location according to the fracability index,
    wherein the computing device performs normalizing and weighting each of the fabric metric and the mineralogic composition metric based on correlations of the fabric metric and the mineralogic composition metric with geo-mechanical properties of reference samples, for estimating the fracability index.

11. The system of claim 10, wherein the electromagnetic probing tool is configured to measure the fabric metric and the mineralogical composition metric for a geological sample.

12. A method for estimating a fracability index for a geological location, the method comprising:
    determining a pore-space metric for a geological sample extracted from a geological location;
    determining a mineralogical composition metric for the geological sample;
    estimating a fracability index for the geological location from the pore-space metric and the mineralogical composition metric; and
    adjusting a hydrocarbon recovery operation for the geological location according to the fracability index,
    wherein the determining of the mineralogical composition metric for the geological sample comprises detecting a prevalence of siliciclastics, carbonate, and clay; and
    wherein the determining of the pore-space metric for the geological sample and/or the determining of the mineralogical composition metric use an electromagnetic probing tool that captures an image of the geological sample, and
    the estimating includes normalizing and weighting each of the fabric metric and the mineralogic composition metric based on correlations of the fabric metric and the mineralogic composition metric with geo-mechanical properties of reference samples.

13. The method of claim 12, wherein the determining of the pore-space metric for the geological sample comprises processing the image of the geological sample.

14. The method of claim 12, wherein determining the mineralogical composition metric for the geological sample comprises detecting a prevalence of at least one organic proxy within the geological sample.

15. The method of claim 12, wherein adjusting the hydrocarbon recovery comprises determining a location for a fracking perforation.

* * * * *